United States Patent [19]

(12) United States Patent
Jalisi et al.

(10) Patent No.: US 8,057,405 B2
(45) Date of Patent: *Nov. 15, 2011

(54) COMPOSITE GUIDEWIRE WITH DRAWN AND FILLED TUBE CONSTRUCTION

(75) Inventors: Marc Mehrzad Jalisi, Temecula, CA (US); David M. Anderson, Temecula, CA (US); Wayne E. Cornish, Fallbrook, CA (US); Nancy A. Nicotra, Temecula, CA (US); Mark T. Richardson, Escondido, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 530 days.

This patent is subject to a terminal disclaimer.

(21) Appl. No.: 12/046,990

(22) Filed: Mar. 12, 2008

(65) Prior Publication Data

US 2008/0200879 A1 Aug. 21, 2008

Related U.S. Application Data

(63) Continuation of application No. 09/470,874, filed on Dec. 22, 1999, now Pat. No. 7,645,242, which is a continuation-in-part of application No. 09/224,453, filed on Dec. 31, 1998, now Pat. No. 6,142,975.

(51) Int. Cl.
*A61B 5/00* (2006.01)

(52) U.S. Cl. ...................................... 600/585

(58) Field of Classification Search .................. 600/585, 600/114, 434; 604/170.01, 107.03, 526
See application file for complete search history.

(56) References Cited

U.S. PATENT DOCUMENTS

| 4,538,622 A | 9/1985 | Samson et al. |
| 4,748,986 A | 6/1988 | Morrison et al. |
| 5,135,503 A | 8/1992 | Abrams |
| 5,341,818 A | 8/1994 | Abrams et al. |
| 5,345,945 A | 9/1994 | Hodgson et al. |
| 5,411,476 A | 5/1995 | Abrams et al. |
| 5,636,641 A | 6/1997 | Fariabi |
| 5,720,300 A | 2/1998 | Fagan et al. |
| 5,776,080 A * | 7/1998 | Thome et al. .................. 600/585 |
| 5,885,381 A | 3/1999 | Mitose et al. |
| 5,951,793 A | 9/1999 | Mitose et al. |
| 7,645,242 B1 * | 1/2010 | Jalisi et al. .................... 600/585 |

FOREIGN PATENT DOCUMENTS

WO WO 96/25969 * 8/1996

* cited by examiner

*Primary Examiner* — Kevin C Sirmons
*Assistant Examiner* — Andrew Gilbert
(74) *Attorney, Agent, or Firm* — Fulwider Patton LLP

(57) ABSTRACT

The present invention is directed to an intracorporeal device, preferably a guidewire, and method for making the device. The guidewire of the present invention is formed, at least in part, of a composite elongate core formed, at least in part, of precipitation hardened material. The elongate core members of the present invention will have an ultimate tensile strength and modulus of elasticity greater than the same for an identically dimensioned elongate member formed from superelastic NITINOL alone.

18 Claims, 2 Drawing Sheets

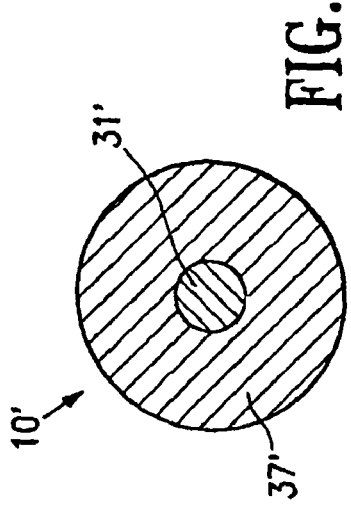
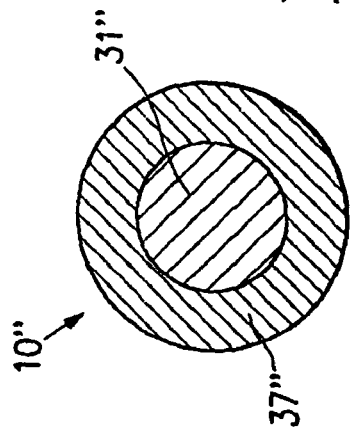
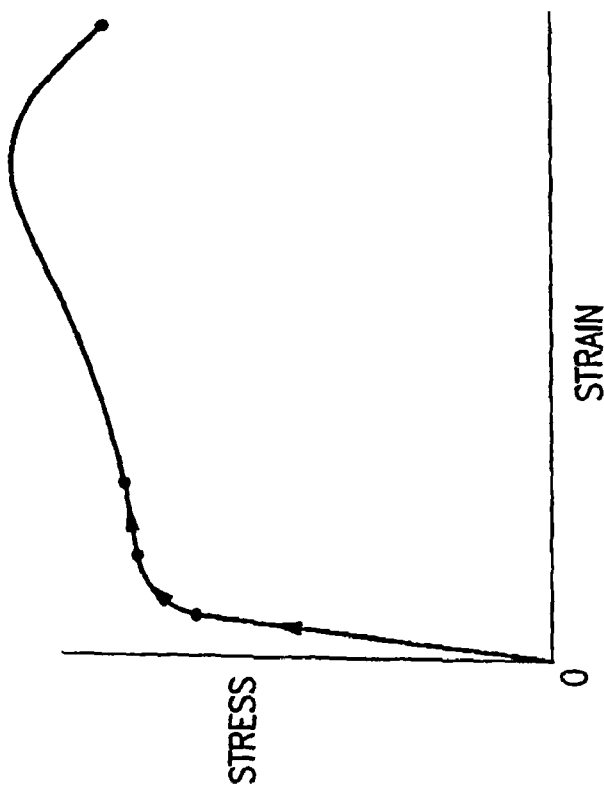

COMPOSITE GUIDEWIRE WITH DRAWN AND FILLED TUBE CONSTRUCTION

CROSS-REFERENCE TO RELATED APPLICATIONS

This application is a continuation of U.S. application Ser. No. 09/470,874, filed Dec. 22, 1999, now U.S. Pat. No. 7,645, 242, which is a continuation-in-part of U.S. application Ser. No. 09/224,453, filed Dec. 31, 1998, now U.S. Pat. No. 6,142, 975, all of whose contents are hereby incorporated by reference.

FIELD OF INVENTION

This invention relates to the field of guidewires for advancing intraluminal devices such as stent delivery catheters, balloon dilatation catheters, atherectomy catheters and the like within body lumens.

BACKGROUND OF THE INVENTION

Conventional guidewires for angioplasty and other vascular procedures usually comprise an elongated core member with one or more tapered sections near the distal end thereof and a flexible body such as a helical coil disposed about the distal portion of the core member. A shapeable member, which may be the distal extremity of the core member or a separate shaping ribbon which is secured to the distal extremity of the core member extends through the flexible body and is secured to a rounded tip at the distal end of the flexible body.

In a typical coronary procedure, a guiding catheter having a preformed distal tip is percutaneously introduced into a patient's peripheral artery, e.g. femoral or brachial artery, by means of a conventional Seldinger technique and advanced therein until the distal tip of the guiding catheter is seated in the ostium of a desired coronary artery. A guidewire is positioned within an inner lumen of a dilatation catheter and then both are advanced through the guiding catheter to the distal end thereof. The guidewire is first advanced out of the distal end of the guiding catheter into the patient's coronary vasculature until the distal end of the guidewire crosses a lesion to be dilated, then the dilatation catheter having an inflatable balloon on the distal portion thereof is advanced into the patient's coronary anatomy over the previously introduced guidewire until the balloon of the dilatation catheter is properly positioned across the lesion. Once in position across the lesion, the procedure is performed.

A requirement for guidewires is that they have sufficient column strength to be pushed through a patient's vascular system or other body lumen without kinking. However, guidewires must also be flexible enough to avoid damaging the blood vessel or other body lumen through which they are advanced. Efforts have been made to improve both the strength and flexibility of guidewires to make them more suitable for their intended uses, but these two properties are for the most part, diametrically opposed to one another in that an increase in one usually involves a decrease in the other.

Further details of guidewires, and devices associated therewith for various interventional procedures can be found in U.S. Pat. No. 4,748,986 (Morrison et al.); U.S. Pat. No. 4,538, 622 (Samson et al.): U.S. Pat. No. 5,135,503 (Abrams); U.S. Pat. No. 5,341,818 (Abrams et al.); and U.S. Pat. No. 5,345, 945 (Hodgson et al.); all of which are incorporated herein in their entirety by reference.

Some guidewires have been formed from a superelastic alloy such as a NITINOL (nickel-titanium or NiTi) alloy, to achieve both flexibility and strength. When stress is applied to NITINOL alloy exhibiting superelastic characteristics at a temperature at or above which the transformation of martensite phase to the austenite phase is complete, the specimen deforms elastically until it reaches a particular stress level where the alloy then undergoes a stress-induced phase transformation from the austenite phase to the martensite phase. As the phase transformation proceeds, the alloy undergoes significant increases in strain but with little or no corresponding increases in stress. The strain increases while the stress remains essentially constant until the transformation of the austenite phase to the martensite phase is complete. Thereafter, further increase in stress are necessary to cause further deformation.

If the load on the specimen is removed before any permanent deformation has occurred, the martensitic phase of the specimen will elastically recover and transform back to the austenite phase. The reduction in stress first causes a decrease in strain. As stress reduction reaches the level at which the martensite phase transforms back into the austenite phase, the stress level in the specimen will remain essentially constant until the transformation back to the austenite phase is complete, i.e. there is significant recovery in strain with only negligible corresponding stress reduction. After the transformation back to austenite is complete, further stress reduction results in elastic strain reduction. This ability to incur significant strain at relatively constant stress upon the application of a load and to recover from the deformation upon the removal of the load is commonly referred to as superelasticity. These properties to a large degree allow a guidewire core of a superelastic material to have both flexibility and strength.

While the properties of the guidewire formed of the superelastic material were very advantageous, it was found that the guidewires and guiding members formed of materials having superelastic characteristics did not have optimum push and torque characteristics.

SUMMARY OF THE INVENTION

The present invention is directed to an intracorporeal device, preferably a guidewire, and method for making the device. The guidewire of the present invention is formed, at least in part, of a composite elongate core member formed, at least in part, of precipitation hardened material. The elongate core members of the present invention will have an ultimate tensile strength and modulus of elasticity greater than the same for an identically dimensioned elongate member formed from superelastic NITINOL alone.

Preferably, the composite elongate core member has a modulus of elasticity of at least $9 \times 10^6$ psi, more preferably, at least $12 \times 10^6$ psi, and most preferably, at least $15 \times 10^6$ psi.

Preferably, the composite elongate core member has a an ultimate tensile strength of at least 150 ksi, more preferably, at least 180 ksi, and most preferably, at least 200 ksi.

In one embodiment, the precipitation hardened material is formed from a material comprising at least two material selected from the group consisting of nickel, cobalt, molybdenum, chromium, tungsten, and iron.

In one embodiment, the precipitation hardened material is formed from a precipitation hardenable stainless steel. Preferably, the precipitation hardenable stainless steel is chromium-nickel based single stage martensitic precipitation hardenable stainless steel. In another embodiment, the precipitation hardenable stainless steel is essentially nickel free.

In another embodiment, the precipitation hardened material is formed from a cobalt based alloy. In one embodiment the cobalt based alloy further includes nickel, molybdenum and chromium while in another embodiment it further includes less than about 10% by wt. iron.

In one preferred embodiment, the composite elongate core member has an inner core element and a first layer portion disposed at least in part about the inner core element, the inner core element and the first layer portion being formed of different material. In an embodiment, the inner core element and the first layer portion are independently formed from superelastic NITINOL and precipitation hardenable material. In another embodiment, the composite elongate core member further includes a second layer portion disposed at least in part about the first layer portion and formed of a material similar to the inner core element material.

In a preferred embodiment, the composite elongate core member includes a distal segment having a distally tapered section with proximal and distal portions, and a distal flexible section, the inner core element being at least partially exposed at the distal flexible section of the distal segment of the composite elongate member.

As is known in the art, many materials used for guidewire construction have desirable mechanical properties, but are difficult to assemble to other guidewire components using conventional technology such as soldering or use of polymer adhesives due to inherent surface properties such as tenacious oxide layers. The construction of guidewires according to the present invention allows the use of materials which have poor bondability or solderability.

The present invention allows for the design of a guidewire with a unitary core, rather than a core with proximal and distal segments joined together. Additionally, the core members of the present invention may be used with other wire designs to create guidewires with improved superelasticity and kink-resistance.

BRIEF DESCRIPTION OF THE DRAWINGS

FIG. 4 is a diagrammatic illustration of a stress-strain curve.

FIG. 5 is a transverse cross sectional view of an alternative guidewire embodying another configuration.

FIG. 6 is a transverse cross sectional view of another alternative guidewire embodying another configuration.

DETAILED DESCRIPTION OF THE INVENTION

Figure 1:
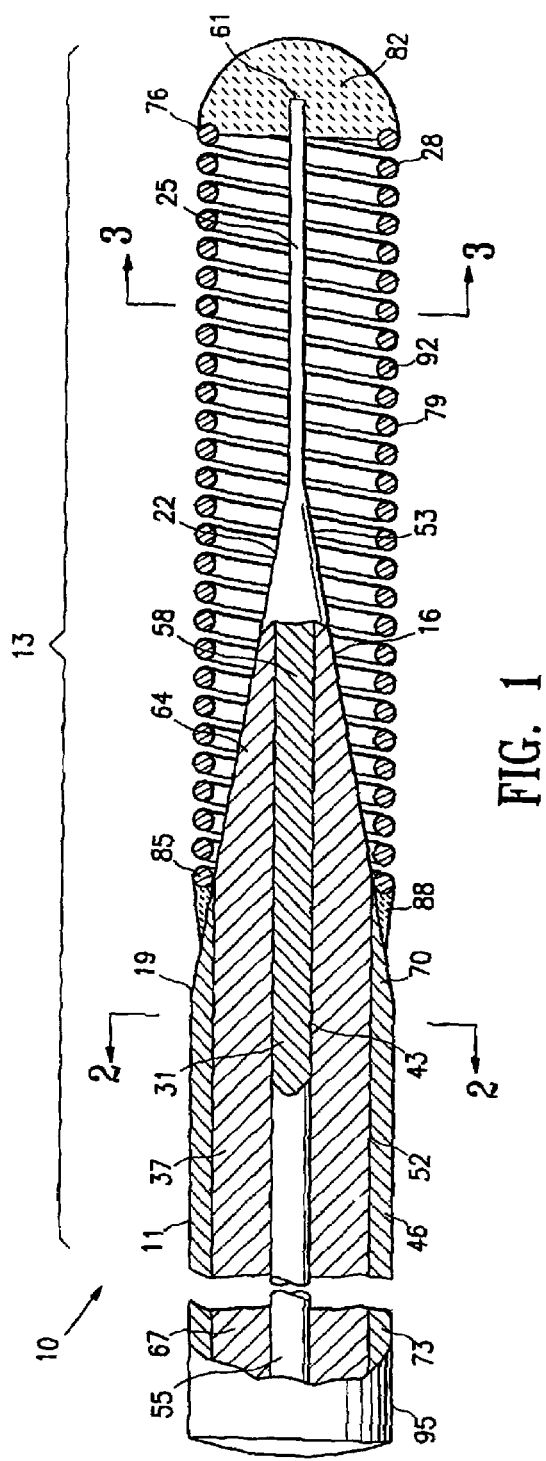
FIG. 1 is a longitudinal cross sectional view of a guidewire embodying features of the invention.
Figure 3:
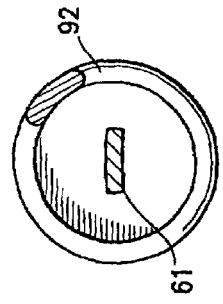
FIG. 3 is a transverse cross sectional view of the guidewire of FIG. 1 taken along line 3-3.
Figure 2:
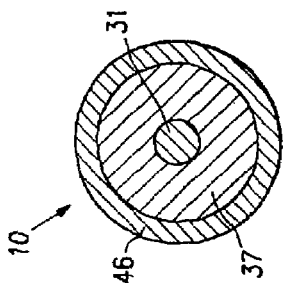
FIG. 2 is a transverse cross sectional view of the guidewire of FIG. 1 taken along line 2-2.

FIGS. 1, 2 and 3 illustrate features of a guidewire 10 embodying the present invention. A composite elongate core member 11 has a distal segment 13 having a distally tapered section 16 with a proximal portion 19, a distal portion 22, and a distal flexible section 25 at a distal end 28 of the guidewire 10 for negotiating the guidewire 10 through the patient's vasculature without causing injury thereto. The distally tapered section 16 can be adjusted in length, taper angle and cross sectional shape to achieve the desired flexibility and performance characteristics for the guidewire 10.

The elongate core member 11 has an inner core element 31 formed from a precipitation hardenable material, a first layer portion 37 formed from a superelastic material disposed on an outer surface 43 of the inner core element 31, and a second layer portion 46 formed from precipitation hardenable material disposed on an outer surface 52 of the first layer portion 37. The inner core element 31 is at least partially exposed at the distal flexible section 25 of the distal segment 13 of the composite elongate member 11. The inner core element 31 may also be exposed at a distal end 53 of the distal portion 22. The first layer portion 37 is at least partially exposed at the distal portion 22 of the distally tapered section 16 of the distal segment 13 of the composite elongate core member 11.

In FIG. 1, The first layer portion 37 and second layer portion 46 are shown as smooth continuous layers. The inner core element 31 has a proximal section 55, a distal section 58 and a distal end 61. The first layer portion 37 has a distal section 64 and a proximal section 67. The second layer portion 46 has a distal section 70 and a proximal section 73.

The distal end 61 of the inner core element 31 is secured to a distal end 76 of a flexible body 79 by a first body of solder 82. A proximal end 85 of the flexible body 79 is secured to the distal section 70 of the second layer portion 46 with a second body of solder 88. Although a single distally tapered section 16 is shown, the distal segment 13 of the elongate core member 11 may have two or more such tapered segments which may or may not be separated by segments of substantially constant diameter. The flexible body 79 is disposed partially about the distally tapered section 16 of the distal segment 13 of the elongate core member 11. The distal flexible section 25 is shown as a flattened portion of the exposed inner core element 31, however, the distal flexible section 25 can have a round cross section, or any other suitable configuration.

The flexible body 79 may be any flexible material such as a helical coil or, a polymer jacket, or the like. Polymers suitable for forming the flexible body 79 include, but are not limited to, polyimide, polyethylene, polyurethane, tetrafluoroethylene (TFE), polytetrafluoroethylene (PTFE), expanded polytetrafluoroethylene (PTFE), and other similar materials. The flexible body 79 in the form of a helical coil 92 (as shown in FIG. 1) may be formed of a suitable radiopaque material such as tantalum, gold, iridium, platinum or alloys thereof or formed of other material such as stainless steel and coated with a radiopaque material such as gold. The wire from which the coil 92 is made generally has a transverse diameter of about 0.001 to about 0.004 inch, preferably about 0.002 to about 0.003 inch. Multiple turns of a distal portion of coil 92 may be expanded to provide additional flexibility. The flexible body 79 may have transverse dimensions about the same as a proximal section 95 of the elongate core member 11. The flexible body 79 may have a length of about 2 to about 40 cm or more, but typically will have a length of about 2 to about 10 cm.

The inner core element 31, at an untapered region such as the proximal section 95 of the elongate core member 11, has a nominal transverse dimension of up to about 0.010 inches, preferably, about 0.003 to about 0.01 inches, and more preferably, about 0.003 to about 0.006 inches. The first layer portion 37 and second layer portion 46, at an untapered region such as the proximal section 95 of the elongate core member 11, each have a nominal wall thickness of up to about 0.015 inches, preferably, about 0.0005 to about 0.01 inches, and more preferably, about 0.001 to about 0.003 inches. Although the inner core element 31 is shown as solid, the inner core element 31 may also be hollow with a lumen extending longitudinally therethrough (not shown) for delivery of diagnostic or therapeutic agents, such as radioactive therapy agents or angiogenic growth factors or the like; or for advancement of elongated medical devices into a patient's vasculature.

The inner core element 31 and the second layer portion 46 may both be formed of precipitation hardened material formed from precipitation hardenable material, with the first layer portion 37 being formed from a superelastic material such as superelastic NITINOL. However, as discussed below, other configurations may also be employed in the practice of the invention.

A significant aspect of the invention resides in forming the composite elongate core member 11, at least in part, from precipitation hardenable material so that the ultimate tensile strength ($\sigma_{uts}$) and tensile yield strength ($\sigma_{ys}$) of the composite (FIG. 4) are raised to enhance the elastic strength and operability of the guidewire, as compared to an elongate core member formed of superelastic NiTi alone.

In an embodiment, features of which are illustrated in FIG. 5 and wherein like references refer to like parts, the guidewire 10' has an inner core element 31' formed from precipitation hardenable material (e.g., precipitation hardenable stainless steel) and a first layer portion 37' formed from superelastic material (e.g., superelastic NITINOL).

In another embodiment, features of which are illustrated in FIG. 6 and wherein like references refer to like parts, the guidewire 10" has an inner core element 31" formed from superelastic material (e.g., NITINOL) and a first layer portion 37" formed from precipitation hardenable material (e.g., precipitation hardenable stainless steel).

Materials suitable for use in the practice of the invention are characterized in that they are precipitation hardenable by controlled heat treatment, not only to increase the ultimate tensile strength of the material but also to increase the tensile yield strength.

The characteristics of the composite elongate core member 11 according to the present invention, without any intention to limit the scope of the invention, may be described as follows:

The ultimate tensile strength and the Young modulus of elasticity for the composite elongated core member are proportional to the cross sectional area of each constituent multiplied by the ultimate tensile strength or the modulus of elasticity, respectively, of that constituent, as defined in Equations I and II, respecitvely:

$$\sigma_{uts\,(C)} = [\sigma_{uts\,(S)} \times (A_{(S)}/A_{(C)})] + [\sigma_{uts\,(Co)} \times (A_{(Co)}/A_{(C)})] \quad \text{Equation I}$$

$$E_{(C)} = [E_{(S)} \times (A_{(S)}/A_{(C)})] + [E_{(Co)} \times (A_{(Co)}/A_{(C)})] \quad \text{Equation II}$$

wherein
$\sigma_{uts}$ is the ultimate tensile strength,
E is the Young modulus of elasticity
A is the cross sectional area,
C is the composite member,
Co is the core,
S is the shell (the shell may, itself, comprise various layers, such as the first and second layer portions).

The foregoing characteristics may be achieved by making the composite elongate core member 11, in part, from a precipitation hardenable material. Example of such precipitation hardenable material include, but are not limited to, AISI (American Iron and Steel Institute) Type 600 series precipitation hardenable stainless steel. Additional examples include chromium-nickel based single stage martensitic precipitation hardenable stainless steel having modified proportions of chromium and nickel and with additional elements of copper and titanium, commercially available from Carpenter Steel Company of Reading, Pa., under the designation 455PH or 17-7PH; and a precipitation hardenable steel available under the trade designation 1RK91 from Sewden Steel.

Other suitable precipitation hardenable stainless steel include those which are essentially "nickel free" such as those sold under the designation BioDur 108, available from Carpenter's Specialty Alloys Operations, Reading, Pa. By way of example, the nominal composition of BioDur is chromium (21%), manganese (23%), nitrogen (1%), nickel (less than 0.3%), and iron (balance).

Other suitable precipitation hardenable material include cobalt based alloys such as those including nickel, cobalt, molybdenum and chromium, also commercially available under the designation MP35N (UNS (Unified Numbering System) R30035) available from Carpenter Steel Co. Also useful in the practice of the invention is a similar alloy that contains a small amount of iron (less than about 10%) and is commercially available under the trade designation Elgiloy (UNS R30003) and L605 from Haynes International of Kokomo, Ind.

The material for forming the first layer portion 37 may be a superelastic alloy, such as superelastic NITINOL (NiTi).

By way of example, the ultimate tensile strength and Young modulus for the composite core member 11 according to FIG. 5, may be calculated using nominal and or preferred values for the ultimate tensile strength and Young modulus for each of the constituents, using Equations I and II, above, and the following parameters:

C has an overall outer diameter of 0.0125 inch,
Co is precipitation hardenable stainless steel (PHSS),
% $A_{(Co)}$=6 to 20%, nominal 12%—equivalent to a core outer diameter of about 0.0045 inch,
S is superelastic NiTi,
% $A_{(S)}$=94 to 80%, nominal 88%, equivalent to a shell wall thickness of about 0.004 inch (0.008 inch total shell thickness),
$E_{(Co)}$=28-30×10$^6$ psi, nominal 28.5×10$^6$ psi, for PHSS; and 33.5-35×10$^6$ psi, nominal 34.5×10$^6$ psi, for cobalt base alloys such as MP35N, L605, and Elgiloy, with less than 10% Iron,
$\sigma_{uts\,(Co)}$=250-330 ksi, preferably ≧280 ksi,
$E_{(S)}$=9-13×10$^6$ psi, nominal 12×10$^6$ for NiTi,
$\sigma_{uts\,(S)}$=160-190 ksi, preferably ≧175 ksi,
$\sigma_{uts\,(C)}$=[$\sigma_{uts\,(S)}$×($A_{(S)}/A_{(C)}$)]+[$\sigma_{uts\,(Co)}$×($A_{(Co)}/A_{(C)}$)]
$\sigma_{uts\,(C)}$=(0.88×175 ksi)+(0.12×280 ksi)=188 ksi
$E_{(C)}$=(0.88×12×10$^6$ psi)+(0.12×28.5×10$^6$ psi)=14×10$^6$ psi As can be seen from the equations and numbers above, the elongate core members of the present invention will have an ultimate tensile strength and modulus of elasticity greater than the same for an identically dimensioned elongate member formed from superelastic NITINOL alone.

The composite elongate core member 11 will preferably have an ultimate tensile strength of at least 150 ksi, more preferably, at least 180 ksi, and most preferably, at least 200 ksi; and a modulus of elasticity greater than 9×10$^6$ psi, more preferably, greater than 12×10$^6$ psi, and most preferably, greater than 15×10$^6$ psi.

The following process is provided, by way of example and not as limitation, to illustrate the method of forming the composite elongate core member 11 of the guidewire 10 in accordance with the invention.

A NiTi alloy tube, for forming the first layer portion 37, having a composition of about 55.9% Ni and 44.1% Ti was drawn to a diameter of about 0.060 inch and an inner diameter of about 0.024 inch. A wire of 17-7PH precipitation hardenable stainless steel was formed with a diameter of about 0.020 inch for forming the inner core element 31. The 17-7PH wire was inserted into the first layer portion 37. A tube of 17-7PH was prepared with an inner diameter of about 0.068 inch and an outer diameter of about 0.114 inch for forming the second outer layer portion 46. The 17-7PH tube for the second layer portion 46 was disposed over the first layer portion 37 (NiTi tube) containing the inner core element 31 (17-7PH wire).

The entire assembly was then drawn in a series of five stages with a 30-60% reduction in cross-sectional area followed by a heat treatment between 600-800° C., in air for about 15 minutes, at each stage. The fifth stage was followed by a sixth stage which included drawing with cold work of about 16% followed by heat treating at a temperature between 400-600° C. and a seventh stage which included drawing with a cold work of about 50% but with no heat treatment. The final cold worked product was aged at a temperature of about 650° C. for about one minute to develop maximum bending, yield, and modulus with minimum springback.

It should be noted that other suitable methods may also be used. For example, the inner core element 31 and the first layer portion 37, and the second layer portion 46, may have different dimensions. Alternatively, the inner core element 31 may be loaded into the first layer portion 37 and cold drawn down to a suitable size prior to insertion into the second layer portion 46. The new assembly can then be drawn down to the desired final size.

While particular forms of the invention have been illustrated and described, it will be apparent that various modifications can be made without departing from the spirit and scope of the invention. Accordingly, it is not intended that the invention be limited, except as by the appended claims.

What is claimed is:

1. A heat-treated elongate member of a guide wire, comprising:
   a composite elongate core;
   the composite elongate core including an inner core having a precipitation hardened material and a layer having a superelastic material arranged concentrically about the inner core; and
   a second layer arranged concentrically about the superelastic layer.

2. The elongate member of claim 1, wherein the composite elongate core has a modulus of elasticity of at least $9 \times 10^6$ psi.

3. The elongate member of claim 2, wherein the modulus of elasticity is at least $12 \times 10^6$ psi.

4. The elongate member of claim 3, wherein the modulus of elasticity is at least $15 \times 10^6$ psi.

5. The elongate member of claim 1, wherein the composite elongate core has an ultimate tensile strength of at least 150 ksi.

6. The elongate member of claim 5, wherein the ultimate tensile strength is at least 180 ksi.

7. The elongate member of claim 6, wherein the ultimate tensile strength is at least 200 ksi.

8. A heat-treated elongate member of a guide wire, comprising:
   a composite elongate core having a proximal section and distal section;
   wherein the composite elongate core includes an inner core having a precipitation hardened material that is surrounded concentrically by a first layer having a superelastic material;
   a second layer disposed at least in part concentrically over the first layer;
   wherein the precipitation hardened material includes at least two materials selected from the group consisting of nickel, cobalt, molybdenum, chromium, tungsten, and iron; and
   a flexible body discrete from the first layer and at least partially overlying the distal section.

9. The elongate member of claim 8, wherein the precipitation hardened material includes precipitation hardened stainless steel.

10. The elongate member of claim 9, wherein the precipitation hardened material includes chromium-nickel based single stage martensitic precipitation hardened stainless steel.

11. The elongate member of claim 9, wherein the precipitation hardened stainless steel is essentially nickel free.

12. The elongate member of claim 9, wherein the precipitation hardened stainless steel includes less than about 1% nickel.

13. The elongate member of claim 8, wherein the precipitation hardened material includes a cobalt based precipitation hardened alloy.

14. The elongate member of claim 13, wherein the cobalt based alloy further includes nickel, molybdenum and chromium.

15. The elongate member of claim 14, wherein the cobalt based alloy further includes less than about 10% by wt. iron.

16. The elongate member of claim 8, wherein the inner core and the first layer are independently formed.

17. The elongate member of claim 8, wherein the second layer is formed from a material similar to the inner core material.

18. A heat-treated elongate member for a guide wire, comprising:
   a composite elongate core;
   the composite elongate core including an inner core including a precipitation hardened material surrounded concentrically by a first layer including a superelastic material and having a proximal section and distal section;
   a second layer at least partially disposed concentrically over the first layer;
   wherein the precipitation hardened material includes at least two materials selected from the group consisting of nickel, cobalt, molybdenum, chromium, tungsten, and iron;
   a flexible body disposed at a distal end of the distal section;
   the distal section having a proximal portion and a tapered distal portion; and
   wherein the precipitation hardened material and superelastic material extend from the proximal section of the elongate core to the tapered distal portion of the distal section of the elongate core and continuing through at least a part of a length of the flexible body.

* * * * *